United States Patent [19]

Takematsu et al.

[11] 4,050,920
[45] Sept. 27, 1977

[54] HERBICIDAL COMPOSITION FOR PADDY FIELD USE

[75] Inventors: Tetsuo Takematsu; Makoto Konnai, both of Utsunomiya; Takayuki Isogawa, Tokyo; Koshiro Kodama, Noshiro, all of Japan

[73] Assignee: Hodogaya Chemical Co., Ltd., Tokyo, Japan

[21] Appl. No.: 617,246

[22] Filed: Sept. 26, 1975

[30] Foreign Application Priority Data

May 8, 1975 Japan .................................. 50-55636
Sept. 26, 1974 Japan ................................ 49-110897

[51] Int. Cl.² .............................................. A01N 9/22
[52] U.S. Cl. ........................................ 71/88; 71/111; 71/118
[58] Field of Search ........................... 71/88, 111, 118

[56] References Cited

U.S. PATENT DOCUMENTS

3,425,820  2/1969  Kawai et al. ........................... 71/106

FOREIGN PATENT DOCUMENTS

47-32645  8/1972  Japan ...................................... 71/111
231,263  11/1968  U.S.S.R. .................................. 71/88

OTHER PUBLICATIONS

Appadurai, Chem. Abst., vol. 71 (1969) 59920w.
Poignant et al., Chem. Abst. vol. 70 (1969) 76628b.

*Primary Examiner*—Lewis Gotts
*Assistant Examiner*—Catherine L. Mills
*Attorney, Agent, or Firm*—Oblon, Fisher, Spivak, McClelland & Maier

[57] ABSTRACT

A herbicidal composition for use in a paddy field comprises 3,4-dichloropropionanilide, S-ethyl-hexahydro-1H-azepine-1-carbothioate and β-naphthyl-N-methyl carbamate.

4 Claims, No Drawings

HERBICIDAL COMPOSITION FOR PADDY FIELD USE

BACKGROUND OF THE INVENTION

1. Field of the Invention

The present invention relates to a herbicidal composition which contains 3,4-dichloropropionanilide as the main active ingredient. More particularly, this invention relates to a herbicidal composition which is effective against weeds indigenous to paddy fields during their growth periods. It is also related to a simple method of effectively weeding by direct sowing flooded paddy fields.

2. Description of the Prior Art

Heretofore, many herbicidal compounds for use in paddy fields have been proposed and applied in practice. Most of these herbicidal compounds have been pre-emergence herbicides. However, in paddy fields, the germination and growth of the various weeds is still vigorous as the activity of the herbicidal compound decreases after the treatment of the pre-emergent herbicides. Accordingly, it is very difficult to effectively control such weeds by using only a pre-emergent herbicide and the optimum weeding technique is therefore to control all weeds at about the time of germination in the paddy fields.

In the past, certain herbicidal compounds have been proposed for treating weeds during their growth periods. 3,4-dichloropropionanilide (hereinafter referred to as DCPA) has been so used throughout the world and is quite effective because it has not phytotoxicity to rice seedlings. However, DCPA will kill all existing barnyard grasses and young broad-leaf weeks. Unfortunately, it is an important condition to obtain the herbicidal effect of DCPA that it be applied only after surface drainage. It is then necessary to prevent watering for a least 2 – 3 days after the foliage treatment. The herbicidal effect of DCPA is not expected when applied while water is in a paddy field because of the resultant dilution of the active ingredient DCPA. In the application of DCPA, it is therefore indispensable to apply it after surface drainage. However, the operation of surface drainage during the middle period after a transplantation is quite disadvantageous for several reasons: rice culture management requires a substantial amount of labor, the fertilizer component is lost by draining, the time for application is necessarily, limited, and replacement of the irrigation water is required after the treatment. Consequently, a need continues to exist for an improved DCPA herbicide.

SUMMARY OF THE INVENTION

Accordingly, it is one object of the present invention to provide a herbicidal composition which is effective for completely controlling grown weeds by application in a flooded paddy field.

It is another object of this invention to provide a herbicidal composition which is effective for completely controlling weeds when applied in a culture by direct sowing in a flooded paddy field.

Briefly, these and other objects of this invention as will hereinafter be made clear by the ensuing discussion, have been attained by providing a herbicidal composition comprising 3,4-dichloropropionanilide (DCPA), S-ethyl-hexahydro-1H-azepine-1-carbothioate (molinate) and β- naphthyl-N-methyl carbamate (β-NAC).

DETAILED DESCRIPTION OF THE PREFERRED EMBODIMENTS

The application of the herbicidal composition of this invention to a flooded paddy field after the growth of weeds has begun will be discussed first.

Suitable ratios of active ingredients for the preparation of the herbicidal compositions of this invention are 50 – 500 g, preferably 100 – 400 g, especially 200 – 300 g of DCPA; 2 – 30g, preferably 5 – 20 g, especially 10 – 17 g of β-NAC; and 50 – 300 g, preferably 150 – 250 g of molinate per 10 ares.

The herbicidal compositions of this invention can be administered in any conventional desired form such as an emulsifiable concentrate, wettable powder granules and the like, depending upon the conditions encountered for treatment. In the preparation of this herbicidal composition, conventional techniques for preparing agrochemical compositions using a carrier inert to all of the active ingredients can be employed. Specific details of the preparation can be determined by conventional considerations. Suitable carriers include liquid carriers such as xylene, isophorone, cyclohexanone, methyl naphthalene, dimethyl formamide and the like; and solid carriers such as bentonite, talc, kaolin clay, diatomaceous earth and the like. It is also possible to include various additives in the compositions, such as emulsifiers, dispersing agents, wetting agents and the like in desirable ratio conventionally determined.

Experiments on the use of the composition of the present invention have shown that it is effective both when the bulk of the flooded water covers all of the weeds and when it covers only 50% of the weeds at a four leaf growth stage. It is preferred to apply the herbicidal composition while the stems and leaves of the weeds are covered with flooded water. Accordingly, the herbicidal composition is especially effective during the middle stage after the transplantation of the rice seedlings. As is clear from illustrations below, the herbicidal compositions of this invention have unique characteristics in that they can completely control barnyard grass, broad leaf weeds and the like during their growth stage in a flooded paddy field. Moreover, no phytotoxicity to rice plants is shown. Accordingly, the herbicidal composition of this invention displays a perfect combination of properties. The practical value of herbicidal compositions of this invention is quite important because of the improvement in agricultural technology which it provides, especially with respect to compatable technology for applying the hebicidal composition in view of the characteristics of its effectiveness. Certain specific advantages of this invention are discussed below.

1. No phytotoxicity to rice plants is found. Pre-emergence herbicides are applied at the time of transplanting of the rice seedlings. This is the time when the seedlings are taking root whereby phytotoxicity is caused. This is a common problem. This phytotoxicity occurs because of the low durability of young rice seedlings and the absorption of the pre-emergence herbicide from the roots. On the other hand, the herbicidal composition of this invention is confirmed to have been demonstrated to be useable without phytotoxicity to rice seedlings even when the leaf stage of the barnyard grass is the same as that of the rice during direct sowing in a flooded paddy field and also when it is higher than the leaf stage of the rice. This is further illustrated by experiments showing that phytotoxicity is not substantially found even after repeated applications of the herbicidal composition of this invention.

2. Barnyard grass, from the germination stage to the four leaf stage, can be completely controlled. Suitable time for application is long. The prior art herbicidal compounds which have been applied in practice in a paddy field, such as Saturn-S, and Swep-M, can be applied at any time up to the two leaf stage of the barnyard grass. In order to control barnyard grass at the three leaf stage or above, it is necessary to apply 1.5 - 2 times of the active ingredient, whereby phytotoxicity to the rice seedlings cannot be prevented. On the other hand, the herbicidal composition of this invention can be applied up to the time of the four leaf stage of the weeds, and can be applied as desired during the middle period after the transplantation of the rice seedlings in the flooded paddy field. Accordingly, the herbicidal compositions of this invention require less labor, providing a concomitant decrease in operating costs.

The combination of DCPA and β-NAC imparts a relatively low herbicidal effect to barnyard grass at a high leaf stage. However, when a small amount of molinate is added to the composition, the time suitable for treatment can be prolonged and a high herbicidal effect can be imparted without failure.

3. Only one application of the herbicidal composition in a paddy field is required. Applications of prior art herbicides in one paddy field have usually been carried out at least 3 to 4 times in practice in paddy fields in Japan. Clearly, such an operation causes a heavy economic and labor level, and increases both the phytotoxicity to the rice, with an attendant decrease in yield, and the resultant chemical residue, caused by application of an excess of chemicals. Furthermore, the germination of weeds in the paddy field continues for a long period of time. Accordingly, the number of applications of the pre-emergence herbicide is increased in order to provide treatment for each germination period of the weeds. On the other hand, by using the herbicidal composition of this invention weeds can be controlled at a desirable period before typical drawbacks caused by weeds ensue such as absorption of fertilizer, provision of light shielding and air flow inhibition, and disease and insect damage. It is clear that controlling weeds after the growth of the main weeds is especially effective. Accordingly, application of the herbicidal composition of this invention during the middle stage after the transplantation of the rice seedlings is effective with low labor cost.

4. Decrease of the herbicidal effect under varying herbicidal conditions does not occur. When only one of the active ingredients of the herbicidal compositions of this invention is applied in an effective amount, herbicidal effect against barnyard grass in its grown stage in a flooded paddy field is not expected and does not occur. However, when the three active ingredients are combined, the effective amounts of any one of the active ingredients is decreased as compared with the amounts required in each combination of two active ingredients. Moreover, the composition of this invention has been found to impart a very remarkable herbicidal effect against barnyard grass which is a principal common weed. Moreover, changes in the herbicidal effect caused by varying temperature, changing depth of the flooded water and water leakage are not substantially found. Thus, a herbicidal effect stable against changes in weather, soil and the like can be attained as one advantageous characteristic of the herbicidal composition of this invention as compared with conventional herbicides. The direct sowing cultivation in flooded paddy fields yields high productivity of labor. However, flooded conditions are usually not uniform since little consideration is given to provision of a uniform level in a paddy field. Accordingly, the depth of water is not uniform and often parts of the paddy field are exposed above water level. Accordingly, different considerations for determining satisfactory herbicidal methods are required as compared with those involved with a perfectly flooded paddy field.

In controlling weeds by direct sowing culture in flooded paddy fields throughout the world, herbicides such as 3,4-dichloropropionanilide (DCPA), S-ethyl-hexahydro-1H-azepine-1-carbothioate (molinate), S-(4-chlorobenzyl) N, N-diethylthiocarbomate (benthiocarb) and the like have been applied. However, the methods of application of these herbicides and the herbicidal effects are not satisfactory. As mentioned above, DCPA is applied after surface drainage. Rainfall is to be avoided after the application in the treatment by DCPA. It is also necessary that irrigation be begun after 3 - 4 days after the treatment, because DCPA is a foliage treating herbicide. On the other hand, molinate or benthiocarb are soil treatment (drench) type herbicides whereby they have to be applied in a flooded condition. But imparting by herbicidal effect on weeds exposed above the water level is most difficult. Accordingly, it is necessary to uniformly level the paddy field after treatment. In order to level a broad area, much labor and time are required and the cost is enormous. Even though a huge investment is made for such leveling, the end result is often most unsatisfactory because uniform leveling is so difficult to attain. When molinate or benthiocarb is used for controlling weeds by direct sowing culture in a flooded paddy field, barnyard grass can be controlled, but herbicidal effect against broad leaf weeds is not substantially found. Even though barnyard grass can be treated, the suitable period for such treatment is limited to the 1 - 1.5 leaf stage. It is difficult to obtain substantial herbicidal effects on 1.5 leaf stage or larger barnyard grass.

In order to overcome these disadvantages, the present herbicidal compositions containing various active ingredients have been developed. In the treatment of the herbicidal composition of this invention by direct sowing culture in a flooded paddy field, a herbicidal composition comprising 50 - 400 g of DCPA, 50 - 400 g of molinate and 0.1 - 1.8 g β-NAC in a form of an emulsifiable concentrate or a wettable powder is applied per 10 ares, by spraying. As stated, flooded conditions are not always uniform thereby exposing certain parts of a field above the water level. Accordingly, it is necessary to use a herbicidal method which is expected to impart uniform herbicidal effect at both the unexposed and the exposed parts of the paddy field. In accordance with this invention, it is possible to impart a herbicidal effect, or inhibit the growth of the weeds by foliage treatment of the composition on the weeds above the water level or on the exposed field. At the same time, the composition falling into the flooded water is distributed in the water such that it is absorbed from the stems, leaves and roots in the flooded water so as to completely control the weeds. In the present invention, the form of the composition can be an emulsifiable concentrate or a wettable powder to allow for spraying of the entire surface involved. Phytotoxicity to the rice is minimized because of the spraying of the entire surface. The herbicidal effect is imparted both above and in the flooded water because of the treatment in a direct sowing culture in the flooded paddy field. As a result, a small ratio of β-NAC to DCPA and molinate should be combined in the formula of the herbicidal composition of this invention. Correspondingly, the active ingredients applied in this invention are 50 - 400 g, preferably 100 - 300 g, especially 200 - 300 g of DCPA; 50 - 400 g, preferably 150 - 250 g of molinate; and 0.1 - 1.8 g, preferably 0.4 - 1.5 g, especially 0.5 - 1 g of β-NAC, per 10 ares.

As is clear from the above statements, it is possible to impart the excellent herbicidal characteristics of the composition of this invention of DCPA, molinate and β-NAC against one to four leaf stage of barnyard grass, broad leaf weeds and umbrella plant (*Cyperus difformis*) during any part of a long suitable period without causing any phytotoxicity to rice seedlings. All the weeds can be completely controlled by application after the growth of the weeds. Long lasting herbicidal action can be effected because of the use of the soil treating type herbicide molinate. Moreover, both a foliage treating herbicidal effect and a water treating herbicidal effect can be imparted making the herbicide of this invention suitable for control of weeds in a direct sowing culture in a flooded paddy field. In addition, such a use is possible because no phytotoxicity to rice seedlings is caused by spraying over all of the surface.

Having generally described the invention, a more complete understanding can be obtained by reference to certain specific examples, which are included for purposes of illustration only and are not intended to be limiting unless otherwise specified.

PREPARATION 1

Preparation of Emulsifiable Concentrate 20 wt. parts of DCPA, 1 wt. part of β-NAC, 7wt. parts of molinate, 62 wt. parts of a mixture of xylene and isophorone (1 : 1) and 10 wt. parts of an emulsifier (Sorpol 800A manufactured by Toho Chemical Co.) were mixed to prepare an emulsifiable concentrate.

PREPARATION 2

Preparation of Wettable Powder 30 wt. parts of DCPA, 1.5 wt. parts of β-NAC, 10 wt. parts of molinate, 53.5 wt. parts of a mixture of bentonite and kaolin (1 : 1) and 5 wt. parts of a dispersing agent (Sorpol 5039) were uniformly mixed to prepare a wettable powder.

PREPARATION 3

Preparation of Granules 10 wt. parts of DCPA, 0.4 wt. part of β-NAC, 7 wt. parts of molinate, 50 wt. parts of bentonite, 29.6 wt. parts of kaolin and 3 wt. parts of a dispersing agent (Sorpol 5060) were mixed and 10 wt. parts of water were added and the mixture was granulated by a granulating machine and was dried to prepare granules.

PREPARATION 4

Preparation of Emulsifiable Concentrate 25 wt. parts of DCPA, 25 wt. parts of molinate, 0.1 wt. part of β-NAC, 25 wt. parts of xylene, 14.9 wt. parts of isophorone and 10 wt. parts of an emulsifier (Sorpol 800-A) were mixed to prepare an emulsifiable concentrate.

PREPARATION 5

Preparation of Wettable Powder 25 wt. parts of DCPA, 25 wt. parts of molinate, 0.07 wt. part of β-NAC, 2 wt. parts of white carbon, 42.93 wt. parts of kaolin clay and 5 wt. parts of a dispersing agent (Sorpol 5039) were uniformly mixed to prepare a wettable powder.

The herbicidal effects of the herbicidal compositions of this invention will be illustrated by the following tests.

EXPERIMENT 1

Test on barnyard grass of various leaf stages in a paddy field

Wagner pots having an area of 1/5000 were filled with soil for paddy fields. Seeds of barnyard grass and broad leaf weeds from a paddy field were sowed, and water was filled with puddling of 3 - 4 cm in depth. Two stands of rice seedlings at the 2.0 - 2.5 leaf stage (Nihonbare) (two seedlings for one stand) were transplanted for growth outdoors. When the barnyard grass has grown to (1) the 3.0 - 3.5 leaf stage or (2) the 3.5 - 4.0 leaf stage, solutions prepared by diluting specific amounts of the herbicidal composition of this invention with water were applied by a pipette without contacting the foliage (stem and leaves) of the plants. After 20 days following the application, the herbicidal effect against the weeds and the degree of damage to the rice plants were observed. On the other hand, as a reference the same application and observations were conducted using reference herbicidal compositions containing two active ingredients. The results and specifics are shown in Table 1. In the tables the ratings are indicated as follows:

| | HERBICIDAL EFFECT |
|---|---|
| 5 | complete control |
| 4 | 80 – 99% control |
| 3 | 60 – 79% control |
| 2 | 40 – 59% control |
| 1 | 20 – 39% control |
| 0 | no effect |

| | PHTOTOXICITY TO RICE |
|---|---|
| ± | quite low damage |
| – | no damage |

TABLE 1

| Herbicidal composition g/10 are | | | (1) Treatment at 3.0–3.5 leaf stage of barnyard grass | | | | (2) Treatment at 3.5–4.0 leaf stage of barnyard grass | | | |
|---|---|---|---|---|---|---|---|---|---|---|
| DCPA | β-NAC | molinate | barnyard grass | umbrella plant | broad leaf weeds | phyto-toxicity to rice | barnyard grass | umbrella plant | broad leaf weeds | phyto-toxicity to rice |
| 300 | 15 | 150 | 5 | 5 | 5 | ± | 5 | 5 | 5 | ± |
| " | 10 | " | 5 | 5 | 5 | – | 5 | 5 | 5 | – |
| " | 5 | " | 5 | 5 | 5 | – | 5 | 5 | 5 | – |
| " | 0 | " | 4 | 4 – 5 | 4 – 5 | – | 4 | 4 | 4 – 5 | – |
| 200 | 15 | 150 | 5 | 5 | 5 | – | 5 | 5 | 5 | – |
| " | 10 | " | 5 | 5 | 5 | – | 5 | 5 | 5 | – |

TABLE 1-continued

| Herbicidal composition g/10 are | | | (1) Treatment at 3.0–3.5 leaf stage of barnyard grass | | | | (2) Treatment at 3.5–4.0 leaf stage of barnyard grass | | | |
|---|---|---|---|---|---|---|---|---|---|---|
| DCPA | β-NAC | molinate | barnyard grass | umbrella plant | broad leaf weeds | phyto- toxicity to rice | barnyard grass | umbrella plant | broad leaf weeds | phyto- toxicity to rice |
| " | 5 | " | 5 | 4 – 5 | 4 – 5 | — | 5 | 4 – 5 | 4 – 5 | — |
| " | 0 | " | 3 | 4 | 4 | — | 3 | 4 | 4 | — |
| 100 | 15 | 150 | 5 | 5 | 5 | — | 5 | 5 | 5 | — |
| " | 10 | " | 5 | 5 | 5 | — | 5 | 5 | 5 | — |
| " | 5 | " | 4 – 5 | 4 | 4 – 5 | — | 4 – 5 | 4 | 4 – 5 | — |
| " | 0 | " | 3 | 4 | 4 | — | 3 | 4 | 4 | — |
| 300 | 15 | 100 | 5 | 5 | 5 | ± | 5 | 5 | 5 | — |
| " | 10 | " | 5 | 5 | 5 | — | 5 | 5 | 5 | — |
| " | 5 | " | 4 – 5 | 5 | 5 | — | 4 – 5 | 5 | 5 | — |
| " | 0 | " | 3 | 4 | 4 – 5 | — | 3 | 4 | 4 | — |
| 200 | 15 | 100 | 5 | 5 | 5 | — | 5 | 5 | 5 | — |
| " | 10 | " | 5 | 4 – 5 | 4 – 5 | — | 5 | 4 | 4 – 5 | — |
| " | 5 | " | 4 | 4 | 5 | — | 4 | 4 | 4 | — |
| " | 0 | " | 3 | 4 | 4 | — | 3 | 4 | 4 | — |
| 100 | 15 | 100 | 5 | 5 | 5 | — | 5 | 5 | 5 | — |
| " | 10 | " | 4 – 5 | 4 | 5 | — | 4 | 5 | 5 | — |
| " | 5 | " | 4 | 4 | 4 – 5 | — | 4 | 4 | 4 | — |
| " | 0 | " | 1 | 3 | 4 | — | 1 | 3 | 4 | — |
| 300 | 15 | 50 | 5 | 5 | 5 | — | 5 | 5 | 5 | — |
| " | 10 | " | 4 – 5 | 4 | 5 | — | 4 | 5 | 4 – 5 | — |
| " | 5 | " | 4 | 4 | 4 | — | 4 | 4 | 4 | — |
| " | 0 | " | 1 | 4 | 4 | — | 1 | 3 | 4 | — |
| 200 | 15 | 50 | 5 | 5 | 5 | — | 4 – 5 | 5 | 5 | — |
| " | 10 | " | 4 – 5 | 4 | 4 – 5 | — | 4 | 4 | 4 | — |
| " | 5 | " | 4 | 4 | 4 | — | 4 | 4 | 4 | — |
| " | 0 | " | 1 | 3 | 3 | — | 1 | 3 | 3 | — |
| 100 | 15 | 50 | 4 | 5 | 4 – 5 | — | 4 | 4 – 5 | 4 – 5 | — |
| " | 10 | " | 4 | 4 | 4 | — | 3 | 4 | 4 | — |
| " | 5 | " | 2 | 4 | 4 | — | 2 | 3 | 4 | — |
| " | 0 | " | 1 | 2 | 2 | — | 0 | 2 | 2 | — |
| 300 | 15 | — | 4 | 4 | 4 – 5 | — | 3 | 4 | 4 – 5 | — |
| " | 10 | — | 3 | 4 | 4 | — | 3 | 4 | 4 | — |
| " | 5 | — | 3 | 3 | 3 | — | 2 | 3 | 3 | — |
| — | 15 | 150 | 3 | 4 | 0 | — | 2 | 4 | 0 | — |
| 200 | 15 | — | 2 | 4 | 4 | — | 2 | 3 | 4 | — |
| " | 10 | — | 2 | 3 | 3 | — | 2 | 3 | 3 | — |
| " | 5 | — | 0 | 2 | 2 | — | 0 | 2 | 2 | — |
| — | 15 | 100 | 1 | 3 | 0 | — | 1 | 3 | 0 | — |

As is clear from Table 1, the herbicidal compositons of this invention can completely control weeds until the 4.0 leaf stage of barnyard grass. Accordingly, the term for treatment can be prolonged until 10 – 20 days following the transplantation of the rice seedlings. The amount of DCPA required can be decreased and only a small amount of DCPA is absorbed from the stems and roots of the rice plants. Accordingly, the application of an insecticidal compound near the time of the application of DCPA can be safe. No phytotoxicity to rice plants was found and it is possible to apply the composition of this invention after the transplanting of young seedlings and to apply it after direct sowing in the flooded paddy field.

EXPERIMENT 2

Tests against weeds in a paddy field at the flooded and growth periods

A paddy field was cultured by a power tiller and puddled to prepare a uniform paddy field. Young seedlings were transplanted by a transplanting machine. Rice seedlings (Nihonbare) at the 2.5 – 3.0 leaf stage were used. After the transplantation of the young seedlings, the paddy field was divided into blocks of area 1 m² with footpath plates in units of two blocks. The granular herbicidal compositions of this invention were applied (1) after 14 days following the transplanting (2.5 – 3.0 leaf stage of barnyard grass) or (2) after 20 days following the transplanting (3.5 – 4.0 leaf stage of barnyard grass). The herbicidal effect and the phytotoxicity to the rice plants were observed after 30 days following the application using the above-mentioned ratings of Experiment 1. As references, other granular herbicidal compositions were also applied. The results are shown in Tables 2 and 3.

TABLE 2

Treatment after 14 days following the transplanting
(2.5 – 3.0 leaf stage of barnyard grass at the time of the treatment)

| Herbicidal composition | | | Amount of comp. per 10 are | Herbicidal effect | | | | Phyto- toxicity to rice |
|---|---|---|---|---|---|---|---|---|
| DCPA | β-NAC | molinate | | barn- yard grass | mono- choria vagin- alis | umbrel- la plant | broad leaf weeds | |
| 10% | 0.4% | 7% | 4 Kg | 5 | 5 | 5 | 5 | — |
| " | " | " | " | 5 | 5 | 5 | 5 | — |
| " | " | " | 3 Kg | 5 | 5 | 4 – 5 | 5 | — |
| " | " | " | " | 5 | 4 – 5 | 4 – 5 | 5 | — |
| Saturn-S granules | | | 4 Kg | 5 | 5 | 5 | 5 | — |

TABLE 2-continued

Treatment after 14 days following the transplanting
(2.5 – 3.0 leaf stage of barnyard grass at the time of the treatment)

| Herbicidal composition | | | Amount of comp. per 10 are | Herbicidal effect | | | | Phyto-toxicity to rice |
|---|---|---|---|---|---|---|---|---|
| DCPA | β-NAC | molinate | | barn-yard grass | mono-choria vagin-alis | umbrel-la plant | broad leaf weeds | |
| (benthiocarb 7% simetryne 1.5%) | | | 3 Kg | 5 | 5 | 5 | 5 | — |
| | | | " | 4 – 5 | 5 | 5 | 5 | — |
| 38-C granules | | | 4 Kg | 4 – 5 | 4 – 5 | 4 – 5 | 5 | — |
| | | | " | 5 | 5 | 5 | 5 | — |
| (DCPA 17% benthiocarb 7%) | | | 3 Kg | 4 – 5 | 5 | 5 | 5 | — |
| | | | | 4 – 5 | 4 – 5 | 4 – 5 | 4 – 5 | |
| | | | " | 4 | 4 | 4 | 4 – 5 | — |

TABLE 3

Treatment after 20 days following the transplanting
(3.5 – 4.0 leaf stage of barnyard grass at the time of the treatment

| Herbicidal composition | | | Amount of comp. per 10 are | Herbicidal effect | | | | Phyto-toxicity to rice |
|---|---|---|---|---|---|---|---|---|
| DCPA | β-NAC | molinate | | barn-yard grass | Mono-choria vacin-alis | umbrella plant | broad leaf weeds | |
| 10% | 0.4 | 7% | 4 Kg | 5 | 5 | 5 | 4 – 5 | — |
| " | " | " | | 4 – 5 | 4 – 5 | 4 – 5 | 4 – 5 | — |
| " | " | " | 3 Kg | 4 | 4 – 5 | 4 | 4 | — |
| | | | | 4 | 4 – 5 | 4 – 5 | 4 | — |
| Saturn-S granules | | | 4 Kg | 3 | 3 – 4 | 3 – 4 | 4 | — |
| | | | " | 2 | 4 | 4 | 4 | — |
| (benthiocarb 7% simetryne 1.5%) | | | 3 Kg | 2 | 3 | 3 | 4 | — |
| | | | " | 1 | 3 | 3 | 3 | — |
| 38-C granules | | | 4 Kg | 2 | 3 | 3 | 4 | — |
| | | | " | 2 | 3 | 3 | 4 | — |
| (DCPA 17% benthiocarb 7%) | | | 3 Kg | 2 | 3 | 3 | 3 | — |
| | | | " | 1 | 3 | 2 | 3 | — |

As is clear from Tables 2 and 3, the granular herbicidal compositions of this invention display high herbicidal effect with phytotoxicity to rice plants in a practical paddy field test. In the treatment during the 3.5 – 4.0 leaf stage of barnyard grass as shown in Table 3, the herbicidal compositions impart a quite high herbicidal effect as compared with Saturn-S granules and 38-C granules as references. The fact that the herbicidal compositions of this invention impart such a high effect on grown weeds, shows the applicability of the compositions over a long period suitable for treatment.

EXPERIMENT 3

Test at the flooded and growth period under water leakage conditions

Wagner pots having an area of 1/2000 were filled with paddy field soil so as to leak water. Seeds of barnyard grass and broad leaf weeds found in a paddy field were sowed on the surface of the soil. Water was added to puddle 3 – 4 cm in depth. Three strands of rice seedlings at 2.5 – 3.0 leaf stage (Nihonbare) (two seedlings for one stand) were transplanted. Water was flooded to a depth of 4 cm after 19 days following the transplanting of the rice seedlings (the 3.5 – 4.0 leaf stage of barnyard grass). The granular herbicidal compositions (Experiment 2) were sowed by hand. Water leakages occured from the next day of the application of the herbicidal composition, at a rate of 3 cm per day, for 1,2 or 3 days. After the water leakage, the growths were effected in 4 cm of water. The herbicidal effect and the phytotoxicity to rice plants were observed after 20 days following the application using the above-mentioned rating of Experiment 1. As references, other granular herbicidal compositions were also applied. The results are shown in Table 4.

TABLE 4

| Composition | Amount (per 10 are) | No water leakage | | 1 day water leakage | | 2 days water leakage | | 3 days water leakage | |
|---|---|---|---|---|---|---|---|---|---|
| | | herbi-cidal effect | phy-to-toxi-city to rice | herbi-cidal effect | phy-to-toxi-city to rice | herbi-cidal effect | phy-to-toxi-city to rice | herbi-cidal effect | phy-to-toxi-city to rice |
| Granules of herbicidal composition of the invention Molinate- *1 | 4 Kg | 5 | — | 5 | — | 5 | — | 5 | — |
| | 3 Kg | 5 | — | 5 | — | 4–5 | — | 4–5 | — |

TABLE 4-continued

| Composition | Amount (per 10 are) | No water leakage | | 1 day water leakage | | 2 days water leakage | | 3 days water leakage | |
|---|---|---|---|---|---|---|---|---|---|
| | | herbicidal effect | phytotoxicity to rice | herbicidal effect | phytotoxicity to rice | herbicidal effect | phytotoxicity to rice | herbicidal effect | phytotoxicity to rice |
| SM granules | 5 Kg | 5 | ± | 5 | ± | 4 | — | 4 | — |
| Saturn-S granules | 5 Kg | 5 | — | 5 | — | 2 | — | 2 | — |

Note:
* 1 molinate 8%, simetryne 1.5%, MCPB 0.8%

As shown in Table 4, the herbicidal effect of the granules of herbicidal composition of this invention does not decrease under the condition of water leakage but still imparts high herbicidal effects. No phytotoxicity to rice plants are found. On the other hand, the herbicidal effect is insufficient by applying the commercial compositions at a ratio of 3 – 4 Kg/10 ares to the 3.5 – 4.0 leaf stage of barnyard grass. Accordingly, the commercial compositions were applied at a ratio of 5 Kg/10 ares. However, a decrease of the herbicidal effect was still present in dependence upon the water leakage condition.

EXPERIMENT 4

In a pot made of polyvinyl chloride having a length of 30 cm, a width of 40 cm, and a height of 7 cm, paddy field soil was filled to form a slanted surface. Paddy field soil containing seeds of barnyard grass, broad leaf weeds, umbrella plant was put on the surface. After applying fertilizer and effecting puddling, rice seeds which were germinated about 1 mm (Nihonbare) were sowed. Management of growth was continued for 8 days in a greenhouse at 20° – 30° C. At the time of the 1 – 1.5 leaf stage of the barnyard grass and 0.8 – 1.2 leaf stage of the rice, water was flooded to produce a flooded condition of 0 – 5 cm of water. The pots were disposed in a frame of 50 cm in length and 50 cm in width. Diluted solutions of the specific amounts of the emulsifiable compositions shown in Table 5 were sprayed by a 15 ml spray gun. The amount of the diluted solution used was 60 liter/10 ares. The herbicidal effect and the phytotoxicity to rice plants were observed after 20 days following the application, using the above-mentioned ratings.

TABLE 5

| Herbicidal composition (g/10 are) | | | Phyto- toxicity to rice | Herbicidal effect | | |
|---|---|---|---|---|---|---|
| DCPA | molinate | -NAC | | barnyard grass | broad leaf weeds | umbrella plant |
| 200 | — | — | — | 3 | 0 | 0 |
| 200 | — | 1.0 | ± | 4.5 | 4 | 2 |
| — | 200 | 1.0 | — | 4 | 0 | 3 |
| 200 | 200 | 0.5 | ± | 5 | 5 | 5 |
| 200 | 150 | 0.5 | ± | 5 | 5 | 4.5 |
| 200 | 150 | 1.0 | + | 5 | 5 | 5 |

As shown in Table 5, when DCPA alone was applied, the herbicidal effect against barnyard grass was not high, and the recovery of growth accrued within a short time. Accordingly, it was ineffective for practical treatment. Moreover, there were no herbicidal effects against broad leaf weeds and umbrella plants. When a combination of DCPA and β-NAC was applied, the herbicidal effect was increased, but complete control of barnyard grass and broad leaf weeds could not be attained. Moreover, the herbicidal effect against umbrella plants was relatively low. When a combination of β-NAC and molinate was applied, a herbicidal effect against broad leaf weeds was not found. However, when the combination of DCPA (200 g/10 are), molinate (150 – 200 g/10 are) and β-NAC (0.5 – 1.0 g/10 are) of this invention was applied, complete control of barnyard grass, broad leaf weeds and umbrella plant was attained. Phytotoxicity to rice plants caused no damage or quite low damage, and the recovery was observed within a short period of time. It is clear from these results that the control of relatively young weeds can be effectively attained even by a direct sowing in a non-uniform flooded condition in accordance with this invention.

EXPERIMENT 5

In accordance with the method of Experiment 4, diluted solutions were prepared by diluting the specific amounts of each composition shown in Table 6. The emulsifiable compositions were sprayed at the time of the 3.5 – 4.0 leaf stage of the barnyard grass and the 3 – 3.5 leaf stage of the rice seedlings by management of the growth for 18 days. The results are shown in Table 6.

TABLE 6

| Herbicidal composition (emulsifiable comp.) | | | Phyto- toxicity to rice | Herbicidal effect | | |
|---|---|---|---|---|---|---|
| g/10 are | | | | barnyard grass | broad leaf weeds | umbrella plant |
| DCPA | molinate | β-NAC | | | | |
| 200 | — | — | — | 2 | 0 | 0 |
| 250 | — | — | — | 3 | 0 | 0 |
| 300 | — | — | — | 3 | 0 | 0 |
| 200 | — | 0.5 | — | 3.5 | 4 | 2 |
| 250 | — | 0.5 | — | 4 | 4 | 2 |
| 300 | — | 0.5 | — | 4 | 4 | 2 |
| 200 | — | 1.0 | — | 4 | 3 | 1 |
| 250 | — | 1.0 | — | 4.5 | 4 | 1 |
| 300 | — | 1.0 | ± | 5 | 4 | 2 |
| — | 200 | 0.5 | — | 3 | 0 | 3 |
| — | 150 | 1.0 | — | 3 | 0 | 2 |
| 200 | 200 | 0.5 | — | 5 | 5 | 5 |
| 200 | 150 | 0.5 | — | 4.5 | 5 | 4.5 |
| 200 | 150 | 1.0 | ± | 5 | 5 | 5 |
| 250 | 200 | 0.5 | ± | 5 | 5 | 5 |
| 250 | 150 | 0.5 | — | 5 | 5 | 5 |
| 250 | 150 | 1.0 | ± | 5 | 5 | 5 |
| 300 | 200 | 0.5 | ± | 5 | 5 | 5 |
| 300 | 150 | 0.5 | — | 5 | 5 | 5 |
| 300 | 150 | 1.0 | ± | 5 | 5 | 5 |

As shown in Table 6, the herbicidal effects of the compositions of this invention were high even by treatment at the grown stage of barnyard grass (3.5 – 4 leaf stage). On the other hand, the phytotoxicity to rice plants was remarkably low as compared with Experiment 4. The durability of the rice seedlings is considered to be high because of the use of a treatment to grown rice seedlings with roots. When DCPA alone was applied, the herbicidal effect was not satisfactory even though the ratio of DCPA was increased from 200 g/10 ares to 300 g/10 ares. The complete control of barnyard grass, broad leaf weeds and umbrella plant could not be attained by the combination of DCPA and β-NAC or the combination of molinate and β-NAC. As is clear from these results, the control of weeds at relatively grown stages can be effectively attained in a culture by direct sowing in a flooded paddy field in accordance with this invention.

Having now fully described the invention, it will be apparent to one of ordinary skill in the art that many changes and modifications can be made thereto without departing from the spirit or scope of the invention as set forth herein.

What is claimed as new and desired to be secured by U.S. Letters Patent is:

1. A method for controlling the growth of weeds in a paddy field which comprises adding a herbicidal composition which comprises 200 – 300 g of 3,4-dichloropropionanilide, 150–250 g of S-ethylhexahydro-1H-azepine-1-carbothioate and 10–17 g of -β-naphthyl-N-methyl carbamate per 10 ares to the water of a flooded paddy field after the growth of weeds has ensued.

2. A method for controlling the growth of weeds in a paddy field which comprises applying a herbicidal composition which comprises 200–300 g of 3,4-dichloropropionanilide, 150–250 g of S-ethyl-hexahydro-1H-azepine-1-carbothioate and 0.5–1.0 g of β-naphthyl-N-methyl carbamate per 10 ares to a flooded paddy field by direct application.

3. The method of claim 2 wherein the herbicidal composition is in the form of an emulsifiable concentrate or a wettable powder.

4. The method of claim 1 wherein the weeds are barnyard grass, broad leaf weeds or umbrella plant.

* * * * *